(12) United States Patent
Msika et al.

(10) Patent No.: US 7,629,371 B2
(45) Date of Patent: Dec. 8, 2009

(54) COSMETIC USE OF A COMPOSITION CONTAINING AT LEAST ONE OXAZOLINE, SERVING AS AN ACTIVE SUBSTANCE, AS A SLIMMING PRODUCT AND/OR FOR PREVENTING AND/OR TREATING CELLULITE

(75) Inventors: Philippe Msika, Versailles (FR); Antoine Piccirilli, Versailles (FR); Nathalie Piccardi, Arceau (FR)

(73) Assignee: Laboratoires Expanscience, Courbevoie (FR)

( * ) Notice: Subject to any disclaimer, the term of this patent is extended or adjusted under 35 U.S.C. 154(b) by 296 days.

(21) Appl. No.: 10/561,173

(22) PCT Filed: Jun. 17, 2004

(86) PCT No.: PCT/FR2004/001504

§ 371 (c)(1),
(2), (4) Date: Dec. 16, 2005

(87) PCT Pub. No.: WO2004/112741

PCT Pub. Date: Dec. 29, 2004

(65) Prior Publication Data

US 2006/0122246 A1    Jun. 8, 2006

(30) Foreign Application Priority Data

Jun. 18, 2003    (FR) .................................. 03 07333

(51) Int. Cl.
*A61K 31/41* (2006.01)
*A61K 31/42* (2006.01)
*A61K 31/421* (2006.01)
*A61K 8/33* (2006.01)
*A61P 17/00* (2006.01)

(52) U.S. Cl. ...................... 514/374; 424/401
(58) Field of Classification Search ................. 514/374; 424/401
See application file for complete search history.

(56) References Cited

U.S. PATENT DOCUMENTS 2,368,075 A * 1/1945 Wampner .................... 424/68
4,876,249 A   10/1989 Rajadhyaksha
5,962,482 A * 10/1999 Bissett ........................ 514/356

FOREIGN PATENT DOCUMENTS

| FR | 2792202 A1 | 10/2000 |
| FR | 2834216 A1 | 7/2003 |
| FR | 2841470 A1 | 1/2004 |
| WO | WO 00/19974 A1 | 4/2000 |

OTHER PUBLICATIONS

Bligh et al., "A rapid method of total lipid extraction and purification," Canadian Journal of Biochemistry and Physiology, The National Research Council of Canada, Aug. 1959, vol. 37, No. 8, pp. 911-917.
Lusskin et al., "A New Reaction of Nitriles. V. Preparation of N-(2-Halo-1-ethyl)-amides," J. Amer. Chem. Soc., 1950, vol. 72, pp. 5577-5578.
Patent Abstracts of Japan, vol. 2003, No. 3, May 5, 2003 (Abstract of JP 2002-338555, Nov. 27, 2002), one page.
Patent Abstracts of Japan, vol. 1998, No. 5, Apr. 30, 1998 (Abstract of JP 10-017565, Jan. 20, 1998), one page.
Patent Abstracts of Japan, vol. 2003, No. 03, May 5, 2003, & JP 2002-338555, Ono Pharaceut Co. Ltd., Nov. 27, 2002, Abstract.
Patent Abstracts of Japan, vol. 1998, No. 05, Apr. 30, 1998, & JP 10-017565, Sankyo Co. Ltd., Jan. 20, 1998, Abstract.

* cited by examiner

*Primary Examiner*—Sreeni Padmanabhan
*Assistant Examiner*—Sahar Javanmard
(74) *Attorney, Agent, or Firm*—Foley & Lardner LLP

(57) ABSTRACT

The invention relates to the cosmetic use of a composition containing at least one oxazoline, serving as an active substance, as a slimming product, and to an associated cosmetic treatment method. The invention also relates to the cosmetic use of a composition containing at least one oxazoline, serving as an active substance, for preventing and/or treating cellulite.

8 Claims, 2 Drawing Sheets

Figure 1:
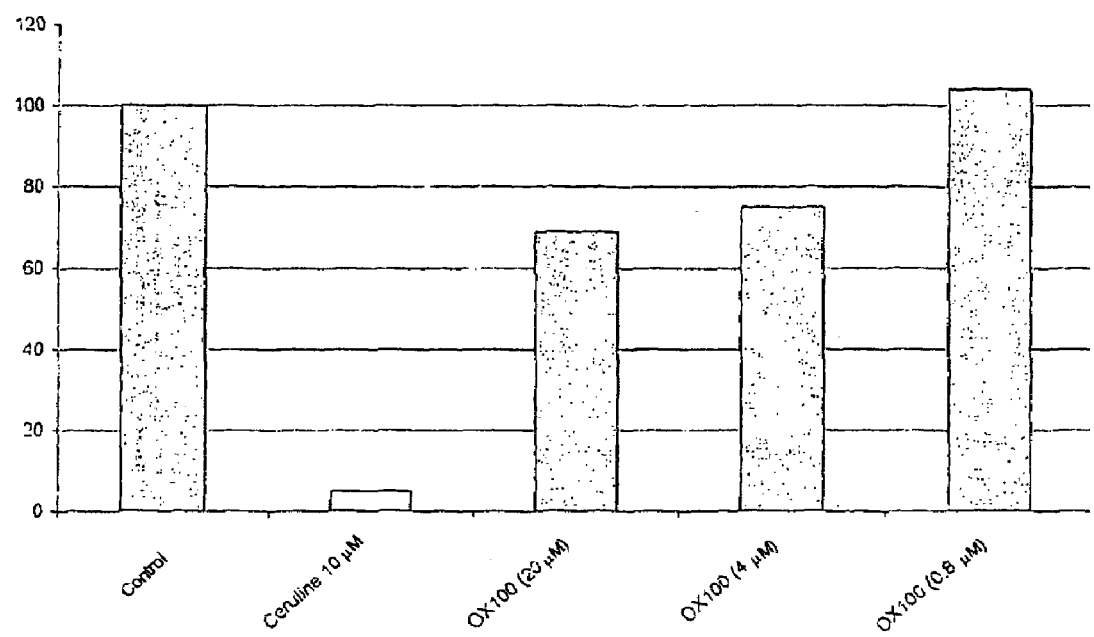

COSMETIC USE OF A COMPOSITION CONTAINING AT LEAST ONE OXAZOLINE, SERVING AS AN ACTIVE SUBSTANCE, AS A SLIMMING PRODUCT AND/OR FOR PREVENTING AND/OR TREATING CELLULITE

The present invention relates to the use of a cosmetic composition with slimming action, comprising, serving as an active substance, at least one oxazoline. The present invention also relates to the use of such a composition for preventing and/or treating cellulitis.

The slimming in the context of the present invention preferentially involves the combating of localized excess weight.

Adiposity, or excess fat in the subcutaneous cellular tissue, can have many causes that are more or less complex, more or less well-known, or more or less understood.

The adipose tissue, a particular variety of connective tissue, consists of adipocytes, separated by partitions, themselves delimited by connective-vascular partitions. The connected component comprises collagen fibers, reticulin fibers and reticuloendothelial cells.

Adipocytes contain varying amounts of fats in the form of triglycerides, these triglycerides being synthesized in vivo by the adipocytes themselves, according to enzymatic-type reactions, from free fatty acids and glycerol, a glucose degradation product, contained in the body and introduced into the latter via food. Now, in parallel, the triglycerides thus formed, and then stored, in the adipocyte cells can also break down again, still under the action of specific enzymes contained in these same cells, this time releasing, firstly, fatty acids and, secondly, glycerol and/or mono- and/or diesters of glycerol. The fatty acids thus released can then either diffuse within the body so as to be consumed or converted therein in various ways, or be taken up again, immediately or a little later, by the adipocytes so as to again generate triglycerides.

The adipocytes therefore store up calories of dietary origin in the form of triglycerides and then convert them to free fatty acids using enzymatic systems. The adipocytes, which thus play an essential role in the synthesis of lipids, their storage and their release into the blood, are regulated by lipogenesis, which corresponds to the formation of triglycerides by enzymatic reaction between fatty acids and glycerol originating from glucose, and lypolysis, which corresponds to the enzymatic breakdown of triglycerides to fatty acids and glycerol.

These conversions take place in particular under the control of mediators such as adrenalin, estrogens, which may or may not block the lipids inside the adipocytes, alpha-receptors, which block lipolysis, and beta-receptors, which facilitate lipolysis.

Cellulitis, or localized lipodystrophy, is characterized by edematous infiltration of the adipose tissue which impairs the attractiveness and harmony of the figure.

If, for various reasons, such as a diet that is too rich, inactivity and/or aging, a substantial imbalance is set up in the body between lipogenesis and lypolysis, i.e. more specifically if the amounts of fats formed by lypogenesis become notable and constantly greater than those that are eliminated by lypolysis, an accumulation of triglycerides then occurs in the adipocytes, which, if it becomes excessive, can result in localized excess weight and/or gradually in the appearance of a thick skin, with a surface that is often uneven, and which has an "orange peel" appearance and a more or less flaccied or gelatinous consistency, in the end giving the figure a generally unsightly appearance.

This cellulitis tissue does not spare men, but is clearly more common in women, whether they are thin or rotund. The fatty masses localize preferentially on the lower half of the body, around the hips, the thighs and the stomach, not forgetting the knees and the ankles.

Cellulitis results in particular from triglyceride storage in the adipocytes, which can increase in volume substantially; in fact, these cells can, depending on the circumstances, reach 40 µm to 120 µm in diameter, i.e. a 27-fold increase in volume, and from an increase in the viscosity of the essential substance of the dermis, which is reflected by water retention and a decrease in cellular exchanges. These two mechanisms result in compression of the blood and lymphatic vessels and tissue congestion.

In order to prevent cellulitis, it is necessary in particular:
to decrease the formation of triglycerides, i.e. to decrease lipogenesis; and/or
to increase lypolysis; and/or
to restore an active and regular microcirculation; and/or
to limit edema.

Given the deep discomfort, both physical and esthetic, and sometimes psychological, that they cause among individuals who are suffering from them, in particular in women, localized excess weight and cellulitis constitute, these days, conditions that people are less and less prepared to put up with or accept.

Methods have already been proposed with a view to treating localized excess weight and cellulitis; among these, some, which are based on surgical treatments, such as liposuction, currently make it possible to obtain results that are truly satisfactory. However, such treatments have, of course, the major drawback that they require subjecting the human or animal body to invasive operations that are by nature delicate, not without risk, and often expensive.

Many slimming cosmetics and/or cosmetics which have an anti-cellulitis action also exist on the market. As examples of active agents commonly used, mention may in particular be made of plant extracts, such as extracts of caffeine, of *Gingko biloba*, of meadowsweet, of *Centalla asiatica*, of *arnica*, of kola nut, of butcher's broom, of English ivy, of rosemary, of marigold, of ginseng, of St John's wort, of cat's whiskers, of brown algae, of red algae, of birch, etc., which are lipolytic agents, and sphingosine and rutin, extracted from *Ruta graveolens*, which are liporeducing agents.

Lipolytic agents act on the elimination of lipid excesses (lipolysis) and liporeducing agents combat the formation of fat (lipogenesis).

These active agents are most commonly administered topically, but they can also be administered per os.

Anti-infiltration active agents, such as *viburnum*, or wild *pansy*, and venotonic agents, such as ruscus or escin, which are often associated with slimming active agents, can be added to these specific active agents.

Finally, the formulations comprising these known slimming and/or anti-cellulitis active agents can be complemented with restructuring and smoothing active agents that combat sagging of the skin.

The cosmetic field is continually in search of novel molecules or novel extracts that are effective in combating human or animal adiposity, with a view in particular to obtaining a general, or conversely localized, slimming effect and/or effect of refinement of the skin or of the figure.

In its French patent application No. 01/16917, the Applicant discloses the use of oxazolines, which make it possible to inhibit the migration of Langerhans cells.

The Applicant thus discloses a medicinal product comprising at least one oxazoline, serving as an active substance, for use in the treatment or prevention of allergic and/or inflammatory and/or irritative reactions of the skin and/or of the mucus membranes.

Patent application U.S. Pat. No. 4,876,249 describes compositions comprising oxazolines, in which the latter are promoters of the penetration of physiological active agents through the stratum corneum layer of the skin.

Surprisingly, the Applicant has discovered that oxazolines are also capable of inhibiting lipogenesis in human adipocytes.

The Applicant has thus discovered that a composition containing at least one oxazoline, serving as an active substance, can be used as a slimming composition, and/or for preventing and/or treating cellulitis.

The oxazolines according to the present invention correspond to the general formulae below:

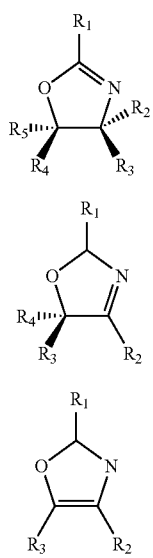

Type 1

Type 2

Type 2 in which $R_1$ represents a linear or branched, saturated or unsaturated $C_1$-$C_{40}$ alkyl group optionally comprising one or more ethylenic unsaturation(s) and also one or more substituent(s) chosen from the group formed by hydroxyl (OH) and $C_1$-$C_6$ alkoxy (OC$_1$-C$_6$) radicals; $R_2$, $R_3$, $R_4$ and $R_5$ represent, independently, a hydrogen atom, a hydroxyl radical, or a linear or branched, saturated or unsaturated $C_1$-$C_{30}$ alkyl group optionally comprising one or more ethylenic unsaturations and also one or more substituent(s) chosen from the group formed by hydroxyl (OH), $C_1$-$C_6$ alkoxy (OC$_1$-C$_6$) and $C_1$-$C_6$ alkoxy carbonyl (COOC$_1$-C$_6$) radicals. The term "$C_1$-$C_6$ alkoxy (OC$_1$-C$_6$)" is intended to mean, for the purpose of the present invention, an alkoxy radical in which the alkyl group contains from 1 to 6 carbon atoms.

According to an advantageous embodiment of the present invention, said oxazoline is a type 1 oxazoline selected from the group composed of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. Advantageously, said oxazoline is 2-undecyl-4,4-dimethyl-1,3-oxazoline, called OX100, of formula:

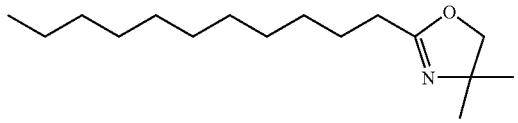

Many synthetic pathways are known for preparing the oxazoline compounds according to the invention. Thus, the latter can be prepared by chemical synthesis by reacting a fatty acid (or a methyl ester) and an amino alcohol, most commonly in the presence of an azeotropic agent in order to promote elimination of the water formed (and of the methanol formed). Another possible synthetic pathway consists in condensing a haloamide in the presence of a strong base or sodium carbonate (R. M. Lusskin, J. Amer. Chem. Soc., 72, (1950), 5577). The oxazolines can also be synthesized by reacting epoxides with nitrites, by reacting thionyl chloride with hydroxyamides, or alternatively by the action of an acid on an aziridinylphosphine.

The expression "slimming" or "combating localized excess weight" is intended to mean, according to the present invention, an action that makes it possible to prevent, or at the very least to reduce, the formation of subcutaneous fats as described above. This action is reflected in particular by a decrease in unsightly excesses or reserves, by slimming down of the figure, by an acceleration in the removal of excesses, by a better definition of the bodyshape or else a reshaped figure.

According to the present invention, the expression "cosmetic treatment method for combating localized excess weight" is intended to mean the use of a cosmetic treatment that makes it possible to visibly measure the action described above.

Thus, a topical composition containing one or more oxazolines used according to the invention can be applied to the areas of the skin liable to form this localized excess weight, namely areas where this excess has already formed or is in the process of being formed.

The cosmetic composition according to the invention is characterized in that the oxazoline concentration is advantageously between approximately 0.01 and approximately 10% by weight, and more advantageously between approximately 0.01 and approximately 3% by weight, relative to the total weight of the composition.

The composition that makes it possible to implement the invention contains a cosmetically acceptable carrier, i.e. a carrier that is compatible with the skin and which is in any of the pharmaceutical forms normally used for topical application, in particular in the form of an aqueous, aqueous-alcoholic or oily solution, of an oil-in-water or water-in-oil or multiple emulsion, of an aqueous or oily gel, of a liquid, pasty or solid anhydrous product, of a dispersion of oil in an aqueous phase by means of spherules, it being possible for these spherules to be polymeric nanoparticles such as nanospheres and nanocapsules or, better still, lipid vesicles of ionic and/or nonionic type, or of a transdermal device, or in any form for topical application.

This composition may be more or less fluid and may have the appearance of a white or colored cream, of an ointment, of a milk, of a lotion, of a serum, of a paste, of a foam or of a gel.

It may optionally be applied to the skin in the form of an aerosol. It may also be in solid form, for example in the form of a stick. It may also be applied by means of a patch.

Advantageously, the cosmetically acceptable medium is an oily solution, a water-in-oil emulsion, an oil-in-water emulsion, a microemulsion, an oily gel, an anhydrous gel, a dispersion of vesicles, of microcapsules or of microparticles, or a transdermal device.

The composition according to the invention may also contain the usual adjuvants in the cosmetic field, such as hydrophilic or lipophilic gelling agents, hydrophilic or lipophilic active agents, thickeners, preserving agents, antioxidants, solvents, fragrances, chelating agents, odor absorbers, chemical or mineral screening agents, mineral pigments, surfactants, polymers, silicone oils and dyestuffs. The amounts of these various adjuvants are those conventionally used in the fields under consideration, and are, for example, from 0.01 to 20% of the total weight of the composition. Depending on their nature, these adjuvants can be introduced into the fatty phase, into the aqueous phase, into the lipid vesicles and/or into the nanoparticles.

When the composition of the invention is an emulsion, the proportion of the fatty phase may range from 5 to 80% by weight, and preferably from 5 to 50% of the total weight of the composition. The oils, the emulsifiers and the coemulsifiers used in the composition in the form of an emulsion are chosen from those conventionally used in the field under consideration. The emulsifier and the coemulsifier are present, in the composition, in a proportion ranging from 0.3 to 30% by weight, and preferably from 0.5 to 20% of the total weight of the composition.

As oils that can be used in the compositions for implementing the invention, mention may be made of mineral oils, oils of plant origin (apricot oil, sunflower oil, plum oil), oils of animal origin, synthetic oils, silicone oils and fluoro oils (perfluoropolyethers). As fats, use may also be made of fatty alcohols (cetyl alcohol), fatty acids, and waxes (beeswax).

As emulsifiers and coemulsifiers that can be used in the invention, mention may, for example, be made of fatty acid esters of polyethylene glycol, such as PEG-40 stearate or PEG-100 stearate, and fatty acid esters of a polyol, such as glyceryl stearate and sorbitan tristearate.

As hydrophilic gelling agents, mention may in particular be made of carboxyvinyl polymers (carbomer), acrylic copolymers such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The methods of administration, the dosages and the optimal pharmaceutical forms of the compounds and compositions according to the invention can be determined according to the criteria generally taken into account in establishing a cosmetic, preferably dermatological, treatment suitable for a patient, such as, for example, the patient's body weight, the fat excess observed, the appearance of the cellulitis tissue, the tolerance to the treatment, and the type of skin.

The composition used according to the invention may contain other active agents with a slimming action, such as the lipolytic agents and the. liporeducing agents as described in the introduction, resulting in an additional or, optionally, synergistic effect.

The invention thus relates to the use of oxazolines, for preparing topical compositions that are useful for preventing and/or treating cellulitis and/or for promoting slimming and in particular for combating localized excess weight, characterized in that one or more oxazolines and also one or more slimming active agents of lipolytic type and/or one or more slimming active agents of liyporeducing type are applied simultaneously, separately or spread out over time.

The slimming active agent of lipolytic type can be chosen from: caffeine, rhodysterol, palmitoylcarnitine, alpha and gamma bioactive agents, escin, *Ginkgo biloba* and sphingosine. The slimming active agent of liporeducing type can be chosen from: andiroba, *Garcinia cambogia* and rutin.

One or more anti-infiltration and/or venotonic active agents can also be applied simultaneously, separately or spread out over time, in addition to the application of the composition used according to the invention. The anti-infiltration or venotonic active agents can be chosen from: *viburnum*, ivy, *arnica*, mouse ear hawkweed, wild *pansy, Fucus vesiculosus*, ruscus, *Ginkgo biloba* and escin.

The composition used according to the invention may also contain other active agents such as:
  an extract of *sophora japonica* flowers; this extract is rich in flavonoids (free-radical scavengers) and in rutin. This active agent promotes the microcirculation, facilitating and activating drainage and anti-infiltration of tissues;
  extract of *centella asiatica*: extract of *centella*, a plant originating from East Africa and from Madagascar. This active agent contains terpenes (asiaticosides, Asiatic acid and madecassic acid), with draining, anti-infiltration and toning activity on tissues. It is in particular used in slimming products but also in anti-stretch mark, anti-wrinkle and healing products; 0 to 5% of extract of *centella* may thus be present in a slimming composition;
  "Hydrolyzed Soy Protein": soy protein which is an elastoregulator. These soy peptides may be any peptide obtained by hydrolysis of proteins extracted from soya, according to operating conditions known to those skilled in the art; in other words, any soy protein hydrolysate. The soy peptides that are disclosed in patent application WO 00/19974 are particularly suitable for being introduced into the compositions used in the context of the present invention. This active agent makes it possible to restore the mechanisms of cell renewal, activates the synthesis of structural elements of the extracellular matrix and has a restructuring, regenerating and toning action; 0 to 5% of soy protein may thus be present in a slimming composition;
  anti-aging and/or toning active agents, among which mention may be made of avocado furans, retinol and its derivatives, vitamin C, vitamin E, silicon, or unsaponifiable soy products, etc.;
  smoothing agents, such as in particular AHA;
  antioxidants;
  active agents capable of blocking the differentiation of preadipocytes to adipocytes, including in particular triterpenes, PPAR (Peroxysome Proliferator-Activated Receptor) antagonists, MMP inhibitors, in particular the peptide extract of lupin as disclosed in French patent application FR 2 792 202;
  active agents for promoting slimming, such as isoflavones, in particular the isoflavones disclosed in French patent application No. 0207995; etc.

A subject of the present invention is also a cosmetic treatment method for promoting slimming, characterized in that a cosmetic composition containing one or more oxazolines is applied topically.

Another subject of the present invention is a cosmetic treatment method for preventing and/or treating cellulitis, characterized in that a composition containing one or more oxazolines is applied topically.

A subject of the present invention is also a cosmetic treatment method for slimming down the figure, accelerating the removal of excesses, and better defining the bodyshape and/or reshaping the figure, characterized in that a composition containing one or more oxazolines is applied topically.

In the context of the present invention, the excess weight is characterized by an excess of weight compared to the non-pathological "ideal weight". The cosmetic treatment according to the invention makes it possible to lose or slim down superfluous localized curves, but is not equivalent to a therapeutic treatment.

According to an advantageous variant of the invention, during these cosmetic treatment methods, one or more oxazolines and also one or more slimming active agents of lipolytic and/or liporeducing type, and/or one or more anti-infiltration and/or venotonic active agents are applied topically to the areas of the skin liable to form localized excess weight, simultaneously, separately or spread out over time.

Figure 2:
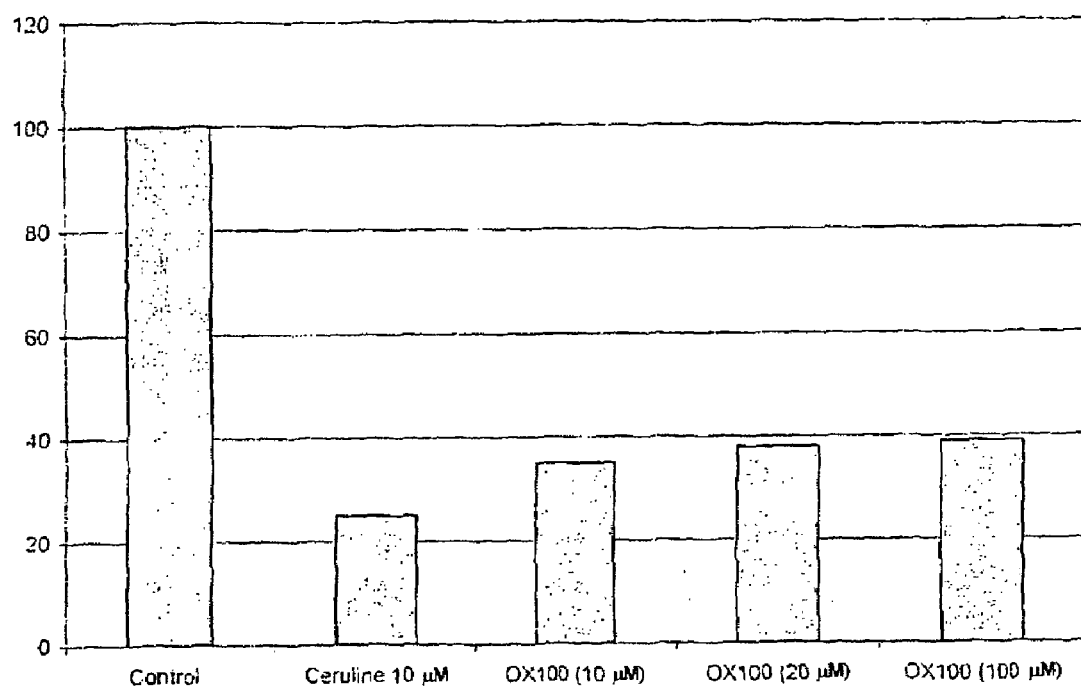

FIGS. 1 and 2 illustrate the effect of OX100 on the incorporation of radiolabelled acetate into adipocyte lipids. The results are expressed as percentage of the control, and represent the incorporation of radiolabelled acetate.

The following examples illustrate the present invention.

EXAMPLE 1

Oil-in-water Cream

| INGREDIENTS | % w/w |
| --- | --- |
| Water | QSF 100 |
| Squalane | 5.00 |
| Petrolatum | 5.00 |
| Glycerol | 5.00 |
| Isodecyl neopentanoate | 5.00 |
| Pentaerythritol tetraethylhexanoate | 5.00 |
| Cyclomethicone | 4.00 |
| Cetearyl alcohol | 3.00 |
| Myristyl myristate | 2.00 |
| Laureth-23 | 2.00 |
| Silica | 2.00 |
| Heptadecadienyl furan | 0.1 to 10 |
| Beeswax | 1.00 |
| Sclerotium gum | 1.00 |
| PEG-6 | 1.00 |
| Polyacrylamide | 0.80 |
| Glyceryl stearate | 0.70 |
| Dimethiconol | 0.70 |
| Cetearyl glucoside | 0.60 |
| C13-14 isoparaffin | 0.40 |
| Citric acid | 0.14 |
| Laureth-7 | 0.10 |
| 4,5,7-Trihydroxyisoflavone | 0.01 to 10 |
| Caffeine | 0.1 to 10 |
| Extract of *Enteromorpha compressa* | 0.01 to 5 |
| Extract of *Garcinia cambogia* | 0.01 to 10 |
| Extract of *Ginkgo biloba* | 0.01 to 10 |
| Extract of *Sophora japonica* flowers | 0.01 to 20 |
| OX100 | 0.01 to 10 |
| Preserving agent | QS |
| Fragrance | QS |

QS = quantity sufficient
QSF = quantity sufficient for

EXAMPLE 2

Water-in-oil Cream

| INGREDIENTS | % w/w |
| --- | --- |
| Water | QSF 100 |
| Hydrogenated polyisobutene | 7.00 |
| Isocetyl stearate | 7.00 |
| Cyclomethicone | 4.80 |
| Glycerol | 4.00 |
| Mineral oil | 3.00 |
| Zinc oxide | 3.00 |
| Butylene glycol | 2.00 |
| Isononyl isononanoate | 2.00 |
| Beeswax | 2.00 |
| Cetyl dimethicone copolyol | 1.70 |
| Polyglyceryl-4 isostearate | 1.65 |
| Hexyl laurate | 1.65 |
| Disodium tartrate | 1.60 |
| Sodium chloride | 1.00 |
| PEG-6 | 1.00 |
| 4,5,7-Trihydroxyisoflavone | 0.01 to 10 |
| Retinyl palmitate | 0.01 to 10 |
| Extract of *Enteromorpha compressa* | 0.01 to 5 |
| Extract of *Sophora japonica* flowers | 0.01 to 20 |
| Extract of *Centella asiatica* | 0.01 to 5 |
| OX100 | 0.01 to 10 |
| Preserving agent | QS |
| Fragrance | QS |

QS = quantity sufficient
QSF = quantity sufficient for

EXAMPLE 3

Stick

| INGREDIENTS | % w/w |
| --- | --- |
| Castor oil | QSF 100 |
| Oleyl alcohol | 20.00 |
| Hydrogenated palm kernel oil | 17.00 |
| Candelilla wax | 11.00 |
| Polyglyceryl-3 beeswax | 10.00 |
| Mineral oil | 9.57 |
| Heptadecadienyl furan | 0.1 to 10 |
| Shea butter | 2.00 |
| 4,5,7-Trihydroxyisoflavone | 0.01 to 10 |
| Quaternium-18 hectorite | 1.10 |
| Titanium dioxide | 1.00 |
| Tocopheryl acetate | 0.50 |
| Propylene carbonate | 0.33 |
| Fragrance | QS |
| Retinol | 0.01 to 10 |
| Extract of *Enteromorpha compressa* | 0.01 to 5 |
| Extract of *Sophora japonica* flowers | 0.01 to 20 |
| Extract of *Centella asiatica* | 0.01 to 5 |
| OX100 | 0.01 to 10 |

QS = quantity sufficient
QSF = quantity sufficient for

EXAMPLE 4

Cream Gel

| INGREDIENTS | % w/w |
| --- | --- |
| Water | QSF 100 |
| Cyclomethicone | 5.40 |
| Octyl palmitate | 5.00 |
| Hydrogenated coco-glycerides | 3.00 |
| Groundnut behenyl alcohol | 2.55 |

-continued

| INGREDIENTS | % w/w |
|---|---|
| Propylene glycol | 2.50 |
| Isodecyl neopentanoate | 2.00 |
| Glyceryl stearate | 1.70 |
| Cetyl alcohol | 1.30 |
| Stearic acid | 1.00 |
| PEG-6 | 1.00 |
| Beeswax | 0.40 |
| C13-14 isoparaffin | 0.40 |
| Butylene glycol | 0.16 |
| Glycerol | 0.16 |
| Cetearyl alcohol | 0.10 |
| Cetyl palmitate | 0.10 |
| Coco-glycerides | 0.10 |
| Laureth-7 | 0.10 |
| 4,5,7-Trihydroxyisoflavone | 0.01 to 10 |
| Extract of Enteromorpha compressa | 0.01 to 5 |
| Extract of Sophora japonica flowers | 0.01 to 20 |
| Extract of Centella asiatica | 0.01 to 5 |
| OX100 | 0.01 to 10 |
| Preserving agent | QS |
| Fragrance | QS |

QS = quantity sufficient
QSF = quantity sufficient for

EXAMPLE 5

Spray

| INGREDIENTS | % w/w |
|---|---|
| Water | QSF 100 |
| Glyceryl | 4.00 |
| Montmorillonite | 3.00 |
| PEG-6 | 3.00 |
| Glycine | 0.30 |
| Citric acid | 0.09 |
| 4,5,7-Trihydroxyisoflavone | 0.01 to 10 |
| Extract of Enteromorpha compressa | 0.01 to 5 |
| Extract of Sophora japonica flowers | 0.01 to 20 |
| Extract of Centella asiatica | 0.01 to 5 |
| OX100 | 0.01 to 10 |
| Preserving agent | QS |
| Fragrance | QS |

QS = quantity sufficient
QSF = quantity sufficient for

EXAMPLE 6

Evaluation of Lipid Synthesis in Adipocytes in Suspension

Product to be Tested

A solution of OX100, diluted to a concentration of $10^{-2}$ M in DMSO, was tested.

Culture Conditions

Normal human adipocytes were isolated from abdominal biopsies (plastic surgery). Immediately after they have been received, the samples are incubated for 30 minutes at 37° C. in the presence of collagenase (supplied by the company Sigma). The adipocyte suspension is subsequently rinsed and diluted three times in the culture medium. The culture medium consists of:

1.87 mg/ml bicarbonate (supplied by the company Life Technologies),

25 IU/ml/25 µg/ml of penicillin/streptomycin (supplied by the company Life Technologies), 2 mM of glutamine (supplied by the company Life Technologies), 100% v/v of MEM (supplied by the company Merck Eurolab), and 0.5% w/v of albumin of bovine origin (supplied by the company Sigma).

Evaluation of Lipid Synthesis

The adipocytes in suspension are incubated for 1 hour at 37° C. in the presence of various concentrations of OX100. The OX100 concentrations tested are 20 µM, 4 µM and 0.8 µM.

A volume of 10 ml of radiolabelled acetate ($2-C^{14}$, 60.87 µCi/ml, supplied by the company Amersham) is subsequently added to the preparation.

After incubation for 4 hours, the lipids are extracted according to the procedure described by Bligh and Dyer, Can J Biochem Physiol, 37, 922, (1959), (methanol/chloroform/water), and evaporated under nitrogen, and the radioactivity incorporated is quantified by liquid scintillation (liquid scintillation device reference LKB 1210, supplied by the company Rackbeta).

The possible interaction between the radiolabelled acetate and the OX100 was evaluated in order to confirm the specificity of labeling, by incubating the highest concentration of OX100 (20 µM) with acetate alone.

Results

OX100 induces no interference with the radiolabelling.

After incubation for 4 hours, the incorporation of $C^{14}$ was increased in the control adipocytes (185 000 cpm). The background noise at T0 was low.

The reference molecule, ceruline (inhibitor of FAS, Fatty Acid Synthase), tested at 10 µM, inhibits the incorporation of acetate (95% inhibition/control). This result validates the test.

OX100 at 20 and 4 µM decreases the incorporation of acetate by, respectively, 31 and 25% of the control (FIG. 1).

It was shown, unexpectedly, that OX100 is capable of inhibiting lipogenesis in human adipocytes.

EXAMPLE 7

Evaluation of Lipid Synthesis in Adipocytes in Suspension

Product to be Tested

A solution of OX100 ($10^{-2}$ M in DMSO) was tested.

Culture Conditions: They are identical to those of example 6.

Evaluation of Lipid Synthesis

The adipocytes in suspension are incubated for 1 h at 37° C. in the presence of various concentrations of OX100 (10, 20 and 100 µMO). A volume of 10 ml of radiolabelled acetate ($2-C^{14}$, 60.87 µCi/ml, Amersham) is subsequently added to the preparation. After incubation for 4 h, the lipids are extracted according to the procedure described by Bligh and Dyer (methanol/chloroform/water), and evaporated under nitrogen, and the radioactivity incorporated is quantified by liquid scintillation (Rackbeta LKB 1210).

Results

OX100 induces no interference with the radiolabelling.

The reference molecule, ceruline (inhibitor of FAS, Fatty Acid Synthase), tested at 10 µM, inhibits the incorporation of acetate (75% inhibition/control). This result validates the test.

OX100 tested at 10, 20 and 100 μM significantly decreases the incorporation of acetate into lipids (respectively, 35, 38 and 39% of the control; FIG. 2).

OX100 showed significant inhibitory activity on lipid synthesis. OX100 is therefore capable of inhibiting lipogenesis in human adipocytes in culture.

The invention claimed is:

1. A treatment method for promoting slimming comprising topically applying on the part of the body to be treated an effective body slimming amount of a composition containing at least one oxazoline, serving as an active agent, for body slimming by inhibiting lipogenesis wherein said oxazoline is a type 1 oxazoline selected from the group consisting of:
   2-undecyl-4-hydroxymethyl-4-methyl-1,3-oxazoline;
   2-undecyl-4,4-dimethyl-1,3-oxazoline;
   (E)-4,4-dimethyl-2-heptadec-8-enyl-1,3-oxazoline;
   4-hydroxymethyl-4-methyl-2-heptadecyl-1,3-oxazoline;
   (E)-4-hydroxymethyl-4-methyl-2-heptadec-8-enyl-1,3-oxazoline; and
   2-undecyl-4-ethyl-4-hydroxymethyl-1,3-oxazoline.

2. The method of claim 1, wherein said oxazoline is 2-undecyl-4,4-dimethyl-1,3-oxazoline, called OX100, of formula:

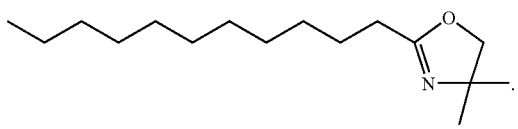

3. The method of claim 1, wherein the composition comprises between 0.01 and 10% by weight of oxazoline, relative to the total weight of the composition, and a cosmetically acceptable medium.

4. The method of claim 1, wherein one or more oxazolines and further one or more slimming active agents of lipolytic type and/or one or more slimming active agents of liporeducing type are applied simultaneously, separately or spread out over time.

5. The method of claim 1, wherein one or more anti-infiltration and/or venotonic active agents are further applied simultaneously, separately or spread out over time.

6. A cosmetic treatment method for slimming down the figure, accelerating the removal of excesses, and better defining the bodyshape and/or reshaping the figure, wherein an effective amount of a composition containing one or more oxazolines, serving as an active agent by inhibiting lipogenesis, is applied topically on the part of the body to be treated, wherein said oxazoline is a type 1 oxazoline selected from the group consisting of:
   2-undecyl-4-hydroxymethyl-4-methyl-1,3-oxazoline;
   2-undecyl-4,4-dimethyl-1,3-oxazoline;
   (E)-4,4-dimethyl-2-heptadec-8-enyl-1,3-oxazoline;
   4-hydroxymethyl-4-methyl-2-heptadecyl-1,3-oxazoline;
   (E)-4-hydroxymethyl-4-methyl-2-heptadec-8-enyl-1,3-oxazoline; and
   2-undecyl-4-ethyl-4-hydroxymethyl-1,3-oxazoline.

7. The cosmetic treatment method as claimed in claim 6, wherein one or more oxazolines and further one or more slimming active agents of lipolytic and/or liporeducing type and/or one or more anti-infiltration and/or venotonic active agents are applied topically to the areas of the skin liable to form localized excess weight, simultaneously, separately or spread out over time.

8. The method of claim 3, wherein the composition comprises between 0.01 and 3% by weight of oxazoline.

* * * * *

UNITED STATES PATENT AND TRADEMARK OFFICE
CERTIFICATE OF CORRECTION

PATENT NO. : 7,629,371 B2  Page 1 of 1
APPLICATION NO. : 10/561173
DATED : December 8, 2009
INVENTOR(S) : Msika et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 615 days.

Signed and Sealed this

Second Day of November, 2010

David J. Kappos
*Director of the United States Patent and Trademark Office*